(12) United States Patent
Alden

(10) Patent No.: US 11,234,784 B2
(45) Date of Patent: Feb. 1, 2022

(54) TENSION REGULATION OF REMOTELY ACTUATED INSTRUMENTS, AND RELATED DEVICES, SYSTEMS, AND METHODS

(71) Applicant: INTUITIVE SURGICAL OPERATIONS, INC., Sunnyvale, CA (US)

(72) Inventor: Donald Alden, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 348 days.

(21) Appl. No.: 16/334,986

(22) PCT Filed: Sep. 21, 2017

(86) PCT No.: PCT/US2017/052638
§ 371 (c)(1),
(2) Date: Mar. 20, 2019

(87) PCT Pub. No.: WO2018/057690
PCT Pub. Date: Mar. 29, 2018

(65) Prior Publication Data
US 2019/0314101 A1  Oct. 17, 2019

Related U.S. Application Data

(60) Provisional application No. 62/398,188, filed on Sep. 22, 2016.

(51) Int. Cl.
*A61B 34/00* (2016.01)
*A61B 17/00* (2006.01)

(52) U.S. Cl.
CPC .... *A61B 34/71* (2016.02); *A61B 2017/00212* (2013.01); *A61B 2017/00371* (2013.01);
(Continued)

(58) Field of Classification Search
CPC combination set(s) only.
See application file for complete search history.

(56) References Cited

U.S. PATENT DOCUMENTS

| 6,394,998 B1 | 5/2002 | Wallace et al. |
|---|---|---|
| 7,736,254 B2 | 6/2010 | Schena |

(Continued)

FOREIGN PATENT DOCUMENTS

| WO | WO-2013190475 A2 | 12/2013 |
|---|---|---|
| WO | WO-2016172299 A1 | 10/2016 |

OTHER PUBLICATIONS

International Preliminary Reporton Patentability for Application No. PCT/US2017/052638, dated Apr. 4, 2019, 13 pages.
(Continued)

*Primary Examiner* — Scott Luan
(74) *Attorney, Agent, or Firm* — Jones Robb, PLLC

(57) ABSTRACT

A surgical instrument includes a shaft with a proximal end and a distal end, a movable component coupled at the distal end of the shaft, a force transmission mechanism coupled at the proximal end of the shaft, and an actuation element with a first end coupled to the force transmission mechanism and a second end coupled to the movable component. The actuation element being configured to transmit an actuation force from the force transmission mechanism to the movable component. A coil spring is coupled to the actuation element between the first and second ends. First and second ends of the coil spring are coupled to longitudinally separated locations on the actuation element. The coil spring is configured to passively expand and contract in response to tension changes in the actuation element. A distance between the longitudinally separated locations changes as the coil spring passively expands and contracts.

19 Claims, 8 Drawing Sheets

(52) U.S. Cl.
CPC .............. *A61B 2017/00477* (2013.01); *A61B 2034/715* (2016.02)

(56) References Cited

U.S. PATENT DOCUMENTS

| | | |
|---|---|---|
| 8,545,515 B2 | 10/2013 | Prisco et al. |
| 8,852,208 B2 | 10/2014 | Gomez et al. |
| 2001/0031983 A1 | 10/2001 | Brock et al. |
| 2006/0084945 A1 | 4/2006 | Moll et al. |
| 2008/0087871 A1* | 4/2008 | Schena .................. F16H 19/06 254/226 |
| 2013/0325031 A1 | 12/2013 | Schena et al. |
| 2013/0325033 A1 | 12/2013 | Schena et al. |
| 2015/0257744 A1* | 9/2015 | Alden .................... A61B 34/30 606/130 |

OTHER PUBLICATIONS

International Search Report and Written Opinion for Application No. PCT/US2017/052638, dated Jan. 9, 2018, 19 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

TENSION REGULATION OF REMOTELY ACTUATED INSTRUMENTS, AND RELATED DEVICES, SYSTEMS, AND METHODS

CROSS-REFERENCE TO RELATED APPLICATIONS

This application is a U.S. national stage application under 35 U.S.C. § 371(c) of International Application No. PCT/US2017/052638, filed on Sep. 21, 2017, which claims priority to U.S. Provisional Application No. 62/398,188, filed Sep. 22, 2016, the entire content each of which is incorporated by reference herein in its entirety.

TECHNICAL FIELD

Aspects of the present disclosure relate to regulating tension in actuation elements of remotely actuated instruments, for example, via one or more tension regulating devices operably coupled to such actuation elements. For example, aspects of the present disclosure relate to tension regulation of actuation elements of remotely-actuatable surgical instruments.

INTRODUCTION

Benefits of minimally invasive surgery are well known, and they include less patient trauma, less blood loss, and faster recovery times when compared to traditional, open incision surgery. Minimally invasive surgery can be performed using remotely-actuated instruments, including both manual (laparoscopic) instruments or instruments operated with computer-assisted, telepresence systems (sometime referred to as robotic surgical systems). Examples of such teleoperated surgical systems (e.g., robotic systems that provide telepresence), such as the da Vinci® Surgical System commercialized by Intuitive Surgical, Inc. of Sunnyvale, Calif. is known. Such teleoperated surgical systems allow a surgeon to operate with intuitive control and with precision.

To perform actions directed by a surgeon, whether manually or teleoperated, some surgical instruments use a force transmission mechanism that receives drive inputs and transmits associated force via actuation elements from a proximal end of the surgical instrument, along its shaft, to an actuatable distal portion of the surgical instrument; for example, to an articulating wrist mechanism and/or an end effector, each having one or more degrees of freedom. In some cases, the actuation elements include tension members, such as cables, wires, or the like. Slack that develops in such actuation elements can affect the transmission of force along such actuation elements. In addition, slack can lead to misalignment and/or derailment of actuation elements, such as, for example, at capstans or pulleys routing the actuation elements in the transmission housing or in the wrist or end effector. It is desirable, therefore, to provide ways to manage slack so as to minimize or prevent misalignment or derailment of actuation elements and/or to provide responsiveness of force transmission from the drive input at the force transmission mechanism, through the actuation elements, and to the ultimate actuation of a distal end portion of the surgical instrument. Some examples of devices configured to manage slack in various ways are shown and described in Int'l Patent App. No. PCT/US2016/028575 (filed Apr. 21, 2016) (disclosing "TENSION REGULATOR FOR ACTUATION ELEMENTS, AND RELATED REMOTELY ACTUATED INSTRUMENTS, SYSTEMS, AND METHODS"), the entire contents of which are incorporated by reference herein in their entirety.

SUMMARY

Various exemplary embodiments of the present disclosure solves one or more of the above-mentioned problems and/or demonstrate one or more of the above-mentioned desirable features. Other features and/or advantages become apparent from the description that follows.

In accordance with at least one exemplary embodiment, a surgical instrument includes a shaft having a proximal end and a distal end, a movable component coupled at the distal end of the shaft; a force transmission mechanism coupled at the proximal end of the shaft, and an actuation element having a first end coupled to the force transmission mechanism and a second end coupled to the movable component. The actuation element is configured to transmit an actuation force from the force transmission mechanism to the movable component. A coil spring is coupled to the actuation element at a location between the first and second ends. First and second ends of the coil spring are coupled to longitudinally separated locations on the actuation element, and the coil spring is configured to passively expand and contract in response to tension changes in the actuation element. A distance between the longitudinally separated locations changes as the coil spring passively expands and contracts.

In accordance with at least another exemplary embodiment, a method of manufacturing a surgical instrument includes coupling first and second ends of a coil spring to longitudinally spaced locations on an actuation element of the surgical instrument. One end of the actuation element is operably coupled to a force transmission mechanism, and a second end of the actuation element is operably coupled to a movable component of the remotely actuatable instrument. The method includes applying a preload tension to the actuation element and in response to applying a preload tension to the actuation element, expanding or contracting the coil spring such that a compressive or tensile force in the coil spring is substantially equal to the preload tension of the actuation element. The longitudinally separated locations are movable with the first and second ends of the coil spring as the coil spring passively expands and contracts.

In accordance with yet another exemplary embodiment, a method of regulating tension in an actuation element of a surgical instrument includes, in response to tension changes in the actuation element, passively expanding or contracting a coil spring positioned around the actuation element and coupled to longitudinally separated locations on the actuation element, and moving the longitudinally separated locations with the first and second ends of the coil spring as the coil spring passively expands or contracts.

In accordance with yet another exemplary embodiment, a surgical instrument includes a proximal drive element, a distal movable component, and an actuation element coupled between the proximal drive element and the distal movable component. A first stop is coupled to the actuation element at a first location and a second stop is coupled to the actuation element at a second location spaced apart from the first location. A spring has a first end engaged with the first stop, a second end engaged with the second stop, and windings that encircle the actuation element between the first and second locations.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

Figure 1:
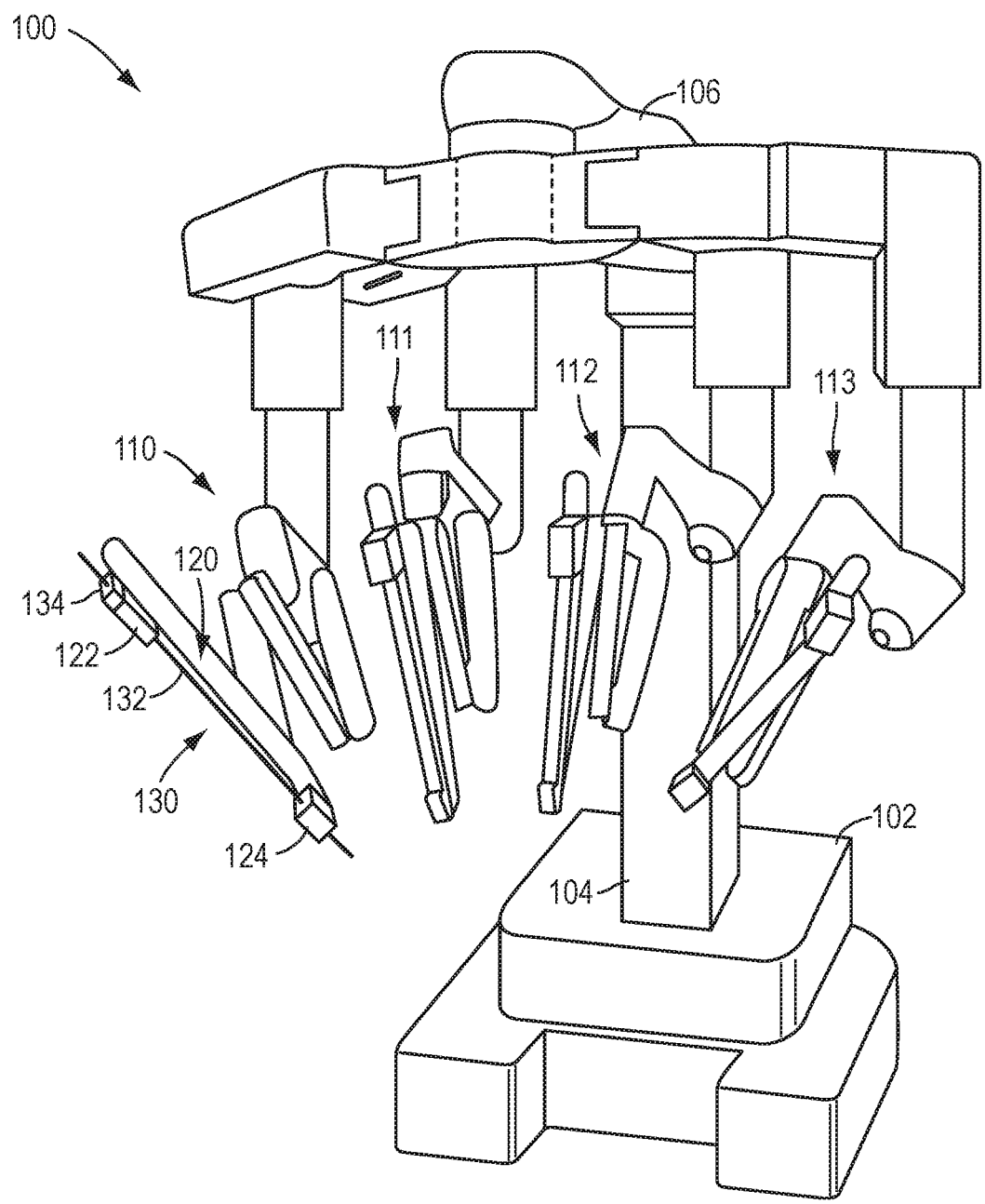
FIG. 1 shows a patient side cart of a teleoperated surgical system, according to an exemplary embodiment.

This description and the accompanying drawings that illustrate exemplary embodiments should not be taken as limiting. Various mechanical, compositional, structural, electrical, and operational changes may be made without departing from the scope of this description and claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the disclosure or claims. For example, spatially relative terms—such as "top", "bottom", "above", "below", "upper", "lower", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

In accordance with various exemplary embodiments, the present disclosure contemplates force transmission mechanisms that include tension regulators that compensate for slack in actuation elements. In various exemplary embodiments, the tension regulators accommodate for slack in a passive manner. For example, tension regulators may utilize potential energy to passively compensate for slack. A tension regulator may passively compensate for slack by changing its configuration or shape (e.g., via elastic deformation) as slack develops in the actuation element. Tension regulators of various exemplary embodiments described herein permit tension in an actuation element to be maintained at a desired or preset level without automated controls or manual adjustments, thus providing an efficient and robust regulation of tension of an actuation element. Therefore, as an actuation element changes over time and develops slack, the tension regulator may compensate for slack and substantially maintain a desired tension in the actuation element, as will be discussed below.

According to an exemplary embodiment, an actuation element follows a substantially straight path as it extends from a transmission mechanism and into the shaft of a surgical instrument. The actuation element may optionally be a pull or pull/pull type actuation element. (A "pull/pull" element is a loop; pulling the loop to rotate clockwise will pull a coupled element in one direction, and pulling the loop to rotate counterclockwise will pull the coupled element in another direction.) In other words, the actuation element is configured to transmit tensile force to actuate the surgical instrument, in contrast to a push/pull type element which transmits both tensile and compressive force to actuate the surgical instrument. Thus, to transmit force to effect motion of different portions of the surgical instrument, the actuation element is generally in a state of tension. As slack occurs in the actuation element, however, in accordance with various exemplary embodiments, a tension regulator coupled to the actuation element accommodates the slack by applying a force inline with (e.g., along a longitudinal axis of) an actuation element. For example, a tension regulator applies an inline force between two locations along the length of the actuation element to shorten a distance between the two locations. Additionally or alternatively, a tension regulator may optionally apply an inline force to alter a length of overlap between portions of an actuation element comprising a first portion and a separate, second portion. Therefore, in an exemplary embodiment, a tension regulator accommodates slack by acting on the actuation element over the portion where slack occurs and exerting a force to maintain tension in that portion. Such tension regulators can serve to reestablish and maintain a tensioned, taut condition of the actuation element. According to an exemplary embodiment, a tension regulator is configured to compensate (e.g., dynamically compensate) for varying amounts of slack (e.g., up to a maximum compensation amount the tension regulator is capable of), such as when the slack of an actuation element increases over time.

A tension regulator may optionally be coupled to an actuation element along a portion of the actuation element that is disposed within a force transmission mechanism and/or a shaft of a surgical instrument. In various exemplary embodiments, a tension regulator is coupled to the actuation element such that the tension regulator moves with the actuation element when the actuation element is actuated according to an exemplary embodiment. In various exemplary embodiments, the tension regulator is configured to float with respect to the force transmission mechanism, (for example, the tension regulator moves with the actuation element relative to the force transmission mechanism). According to an exemplary embodiment, a tension regulator is coupled to one or more of a plurality of actuation elements connected to an actuation input mechanism.

A portion of an actuation element extending through a tension regulator may optionally be a continuous length portion of the actuation element, according to an exemplary embodiment. In other words, in an exemplary embodiment, the tension regulator takes up slack by acting on a portion of a length of the actuation element between ends of the actuation element, as opposed to, for example, acting on an end of the actuation element. According to another exemplary embodiment, the tension regulator takes up slack by acting on ends of respective, separate segments of an actuation element, an opposite end of each of the separate segments making up the overall length of the actuation element through which force is transmitted.

Although various exemplary embodiments described herein are discussed with regard to surgical instruments used with a teleoperated surgical system, the present disclosure is not limited to use with surgical instruments for a teleoperated surgical system. For example, various exemplary embodiments of tension regulators described herein can be used in conjunction with hand-held, manual surgical instruments. In addition, various exemplary embodiments can be used with remotely-actuatable instruments configured for non-surgical applications, such as in various other robotic manipulator applications or otherwise.

Referring now to FIG. 1, an exemplary embodiment of a patient side cart 100 of a teleoperated surgical system is shown. A teleoperated surgical system may optionally further include a surgeon console (not shown) for receiving input from a user to control instruments mounted at patient side cart 100. A teleoperated surgical system also can optionally include an auxiliary control/vision cart (not shown), as described in, for example, U.S. Patent App. Pub. No. US 2013/0325033 A1 (filed May 31, 2013) entitled "Multi-Port Surgical Robotic System Architecture", U.S. Patent App. Pub. No. US 2013/0325031 A1 (filed May 31, 2013) entitled "Redundant Axis and Degree of Freedom for Hardware-Constrained Remote Center Robotic Manipulator," and U.S. Pat. No. 8,852,208 (filed Aug. 12, 2010) entitled "Surgical System Instrument Mounting," each of which is hereby incorporated by reference in its entirety. Further, exemplary embodiments described herein can be used, for example, with a da Vinci® Surgical System, such as the da Vinci Si® Surgical System or the da Vinci Xi® Surgical System, both with or without Single-Site® single orifice surgery technology, all commercialized by Intuitive Surgical, Inc. But, those having ordinary skill in the art would appreciate that other surgical systems are contemplated as being used in conjunction with the tension regulators and surgical instruments of the present disclosure. Additionally, one or more controllers and processors can be included in other components of a surgical system, such as for example the patient side cart and/or surgeon console, rather than as part of a separate auxiliary/control cart. Control and processing architecture can also be distributed between various components of the surgical system as those having ordinary skill in the art would appreciate.

According to an exemplary embodiment, patient side cart 100 includes a base 102, a main column 104, and a main boom 106 connected to the main column 104. The patient side cart 100 also includes a plurality of teleoperated manipulator arms 110, 111, 112, 113 (sometimes referred to as patient side manipulators), which are each connected to the main boom 106, as depicted in the exemplary embodiment of FIG. 1. Manipulator arms 110, 111, 112, 113 each include an instrument mount portion 120 to which an instrument 130 is mounted, which is illustrated as being attached to manipulator arm 110. Portions of the manipulator arms 110, 111, 112, 113 are manipulated during a surgical procedure according to commands provided by a user at the surgeon console. In an exemplary embodiment, signal(s) or input(s) transmitted from a surgeon console are transmitted to the control/vision cart, which interprets the input(s) and generate command(s) or output(s) to be transmitted to the patient side cart 100 to cause manipulation of an instrument 130 (only one such instrument being mounted in FIG. 1) and/or portions of manipulator arm 110 to which the instrument 130 is coupled at the patient side cart 100.

Instrument mount portion 120 comprises an actuation interface assembly 122 and a cannula mount 124. A shaft 132 of instrument 130 extends through a cannula 136 coupled to cannula mount 124, and on to a remote site during a surgical procedure. A force transmission mechanism 134 at a proximal end of instrument 130 is mechanically coupled with the actuation interface assembly 122, according to an exemplary embodiment. Persons having ordinary skill in the art are familiar with surgical instrument force transmission mechanisms, which receive a mechanical input force from a source (e.g., an electric motor on a manipulator arm supporting the instrument) and convert and/or redirect the received force to an output force to drive a component (e.g., a wrist, an end effector, etc.) at a relatively distal end portion of the instrument. Cannula mount 124 is configured to hold a cannula 136 through which shaft 132 of instrument 130 extends to a surgery/treatment/diagnosis site during a surgical procedure. Actuation interface assembly 122 contains a variety of drive and other mechanisms that are controlled to respond to input commands at the surgeon console and transmit force to the force transmission mechanism 134 to actuate instrument 130, as those skilled in the teleoperated surgical system art are familiar with.

Although the exemplary embodiment of FIG. 1 shows an instrument 130 attached to only manipulator arm 110 for ease of illustration, one or more additional instruments may be attached to any one of a respective manipulator arm, e.g., any one of manipulator arms 110, 111, 112, 113. An instrument 130 may be a surgical instrument with an end effector such as forceps or graspers, a needle driver, a scalpel, scissors, a stapler, a clamp, a cauterizing tool, etc., or may optionally be an endoscopic imaging instrument or other sensing instrument used during a surgical procedure to provide information (e.g., visualization, electrophysiological activity, pressure, fluid flow, and/or other sensed data) sensed at a surgical site. In the exemplary embodiment of FIG. 1, a surgical instrument with an end effector or a sensing instrument may be attached to and used with any of manipulator arms 110, 111, 112, 113. The embodiments described herein are not limited to the exemplary embodiment of the patient side cart of FIG. 1, however, and various other teleoperated surgical system configurations, including patient side cart, table-mounted, and ceiling-mounted configurations, may be used with the exemplary embodiments described herein.

Figure 2:
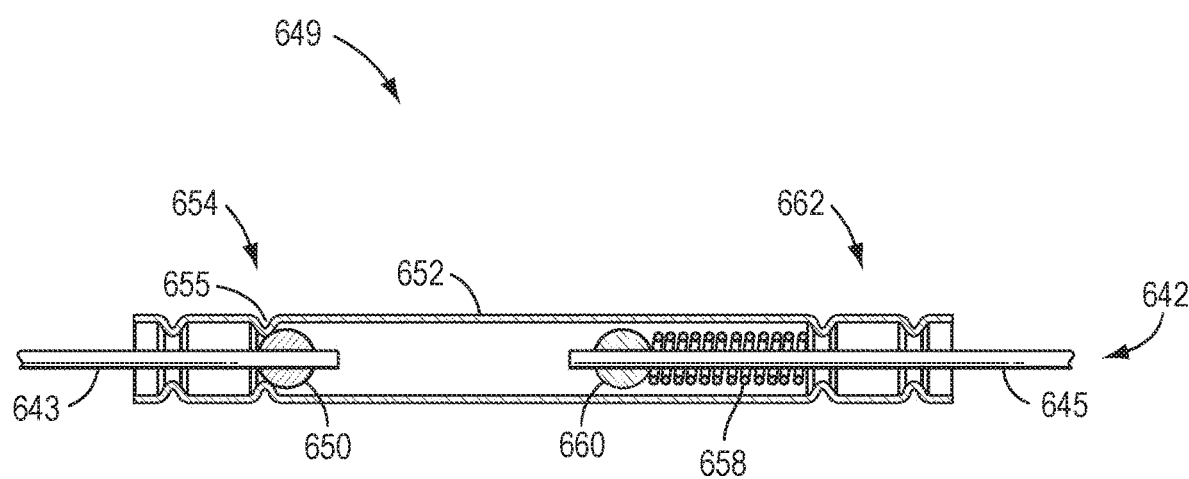
FIG. 2 is a cross-sectional view of a prior art cable tension device.

Referring to FIG. 2, a prior-art tensioning device 649 is shown. An actuation element 642 includes a first segment 643 and a second segment 645. The first segment of the actuation element 643 includes a stop (e.g., ball end 650, barrel end, etc.) disposed within a first end 654 of a tube 652. A narrowed portion (e.g., a crimp) 655 in the tube 652 holds the stop 650 within the first end 654 of the tube 652. A compression spring 658 is disposed between a ball end 660 on the second segment 645 of the actuation element 642 and a second end 662 of the tube 652.

The actuation element 642 is pre-tensioned such that the compression spring 658 is fully compressed on installation, and as the actuation element 642 (e.g., first segment 643 and second segment 645) stretches through use, the compression spring 658 extends to take up slack in the actuation element 642.

Compared to the prior-art device shown in FIG. 2, exemplary embodiments of the present disclosure include fewer component parts and enable simplified assembly (e.g., fewer and/or less complicated assembly operations), thereby reducing the cost of manufacturing and materials. Additionally, tension regulators according to some exemplary embodiments of the disclosure occupy less space within a surgical system than the prior art device of FIG. 2. Further, the exemplary embodiments of the present disclosure improve robustness and reliability of devices and systems in which actuation elements with tension regulators of the present disclosure are included.

Figure 3:
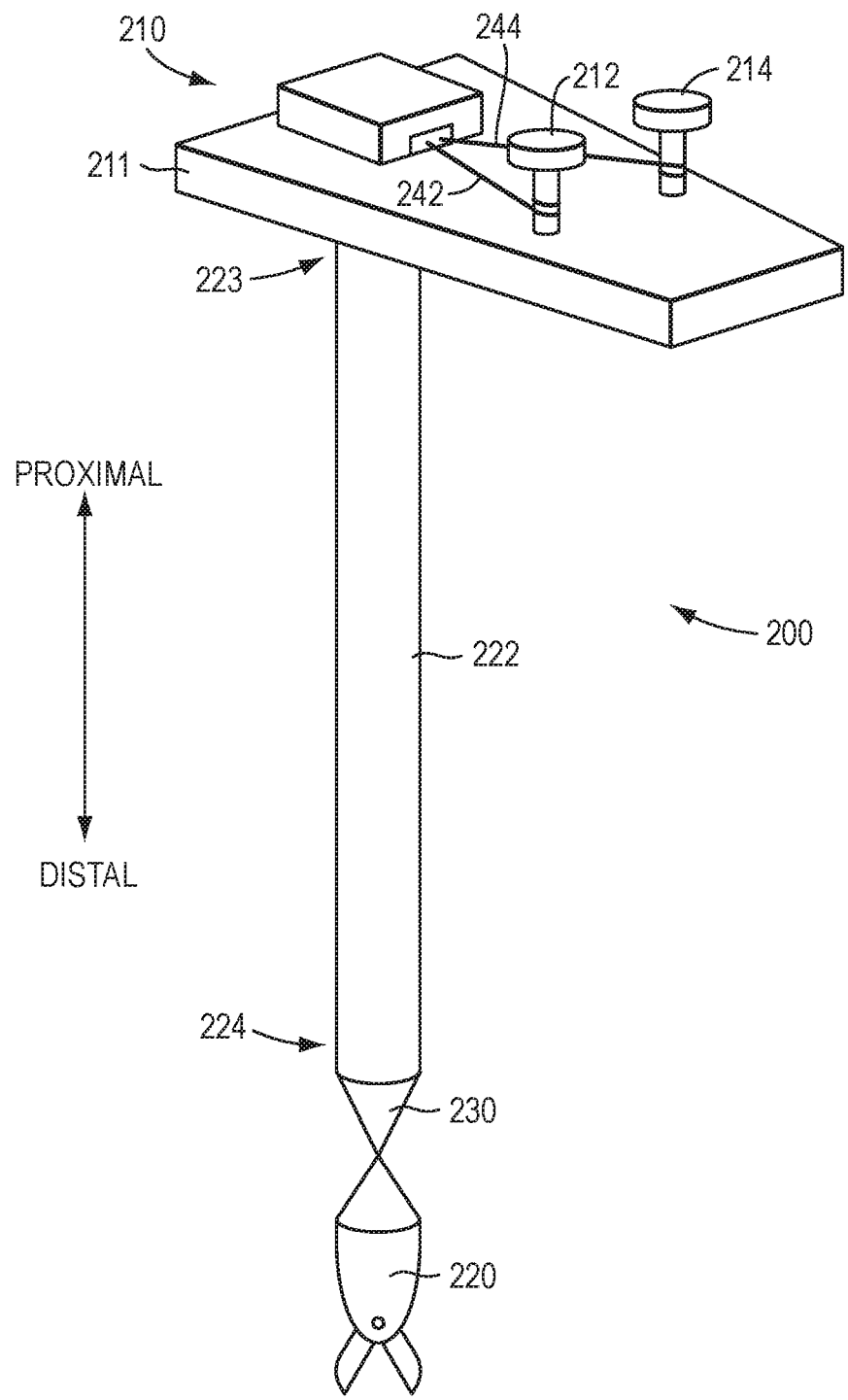
FIG. 3 is a diagrammatic perspective view of a surgical instrument, according to an exemplary embodiment.

Turning to FIG. 3, a diagrammatic perspective view of an exemplary embodiment of a surgical instrument 200 is shown. For instance, surgical instrument 200 is used as the instrument 130 with the patient side cart 100 of the exemplary embodiment of FIG. 1. Surgical instrument 200 includes a force transmission mechanism 210 (a chassis 211 for which is shown in the exemplary embodiment of FIG. 3, with a housing being removed from the illustration so as reveal components of the force transmission mechanism 210 within), a shaft 222 connected to force transmission mechanism 210 at a proximal end 223 of shaft 222, a wrist 230 connected to a distal end 224 of shaft 222, and an end effector 220 connected to wrist 230. Shaft 222 may be flexible or rigid. Although a jawed mechanism is illustrated in FIG. 3, the end effector 220 may comprise, for example, any of the end effector configurations listed above.

Surgical instrument 200 includes one or more members to translate force between force transmission mechanism 210 and end effector 220 and/or between force transmission mechanism 210 and wrist 230. For example, actuation elements 242, 244 operably couple the force transmission mechanism 210 to end effector 220 to provide actuation forces to end effector 220, such as by extending through an interior of shaft 222. By utilizing actuation elements 242, 244, force transmission mechanism 210 actuates end effector 220 to control, for example, a jaw of end effector 220 (or other moveable part of end effector 220). In another example, actuation elements 242, 244 may optionally be utilized to actuate wrist 230 in one or more degrees of freedom (e.g. pitch and/or yaw). In the exemplary embodiment of FIG. 3, actuation elements 242, 244 are in the form of tension members, such as when force transmission mechanism 210 is a pull or pull/pull mechanism, as described in U.S. Pat. No. 8,545,515 B2 (filed Nov. 13, 2009), which is hereby incorporated by reference in its entirety.

Force transmission mechanism 210 includes one or more components to engage with a patient side cart 100 of a teleoperated surgical system to translate a force provided by patient side cart to surgical instrument 200. For example, in an exemplary embodiment, force transmission mechanism 210 connects with the actuation interface assembly 122 of the patient side cart 100 of the exemplary embodiment of FIG. 1 permitting actuation interface assembly 122 to transmit force to force transmission mechanism 210 to actuate instrument 200. According to an exemplary embodiment, force transmission mechanism 210 includes one or more driven actuation input mechanisms 212, 214 that engage (e.g., via a force or torque transmission interface (gimbals, levers, sliding tabs, rotating disks, and the like) at the distal end of force transmission mechanism 210) with a manipulator of a patient side cart, such as actuation interface assembly 122 of patient side cart 100.

According to an exemplary embodiment, actuation input mechanisms 212, 214 interact with a manipulator of a patient side cart, such as actuation interface assembly 122 of patient side cart 100, via a sterile adapter (not shown), as will be described below. According to an exemplary embodiment, force transmission mechanism 210 is a pull or pull/pull mechanism, actuation elements 242, 244 are tension members, and driven actuation input mechanisms 212, 214 are capstans that are rotationally driven by actuation interface assembly 122 to tension actuation elements 242, 244 to actuate instrument. Thus, driven actuation input mechanisms 212, 214 utilize actuation forces from an actuation interface assembly to actuate instrument 200. Force transmission mechanism 210 optionally include other components in addition to or in lieu of capstans to actuate various other functionalities of a surgical instrument, as those having ordinary skill in the art are familiar with. Such components include, but are not limited to, gears, clutches, pulleys, linkages, and other mechanisms to convert input force and/or motion into a desired output force and/or motion. Further, force transmission mechanism 210 optionally include other numbers of actuation input mechanisms 212, 214 than shown in the exemplary embodiment of FIG. 3, such as, for example, one, three, four, five, six, seven, eight or more actuation input mechanisms. For example, any number of actuation input mechanisms 212, 214 can be used, depending on the nature of a particular surgical instrument and depending upon the degrees of operational freedom of such an instrument.

The force transmission mechanism of FIG. 3 provides an accurate conversion of rotational movement to translation movement of an actuation element for a surgical instrument of a teleoperated surgical system. However, actuation elements of a force transmission mechanism can experience a change in shape. For example, in some cases, actuation element 242 of the exemplary embodiment of FIG. 3, which is a tension member, deforms, such as by stretching and increasing in length in proportion to a load delivered. As a result, actuation element 242 develops slack, e.g., through repeated use. Actuation element 244 moves in coordination with actuation element 242 if both are coupled to a movement of the wrist 230 or end effector 220. With such coordinated movement, actuation element 244 also develops slack. Conversely, actuation element 242 could be in tension, with actuation element 244 having slack. Further, when actuation elements 242, 244 are in a state of slack, the precision of force transmission mechanism 210 to actuate instrument 200, such as by movement of end effector 220 or wrist 230, diminishes. For instance, the driven actuation input mechanisms 212, 214 may need to be rotated to remove slack from actuation elements 242, 244 in order to place the actuation elements 242, 244 in a taut state in which they can actuate the instrument 200. In addition, driven actuation input mechanisms 212, 214 optionally include a groove (not shown) in which the actuation elements 242, 244 normally lie during use of force transmission mechanism 210. Slack in actuation elements 242, 244 could become significant enough that actuation elements 242, 244 move out of the groove, which can also affect the actuation of instrument 200. Therefore, further improvements can be made with surgical instrument components to compensate for changes in actuation elements, such as by using tension regulation devices that utilize the limited space within a surgical instrument in a more efficient way.

Figure 4:
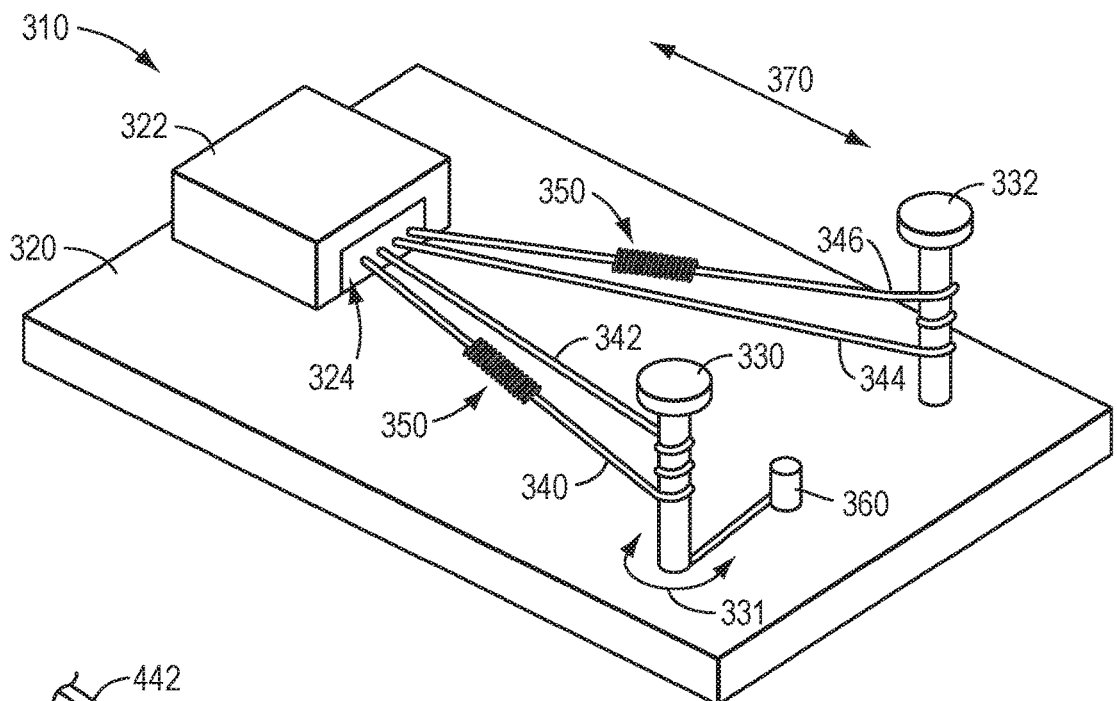
FIG. 4 is a perspective view of an interior portion and chassis of a force transmission mechanism, according to an exemplary embodiment.

Turning to FIG. 4, an interior portion of a force transmission mechanism 310 is shown, according to an exemplary embodiment. Force transmission mechanism 310 comprises a chassis 320 and a housing (not illustrated to reveal components of force transmission mechanism 310 within) covering the internal components mounted to the chassis 320. Force transmission mechanism 310 is used as transmission mechanism 134 of instrument 130 of the exemplary embodiment of FIG. 1. According to an exemplary embodiment, force transmission mechanism 310 also comprises other components, such as, for example, a roll gear (not shown) to engage a proximal portion of a shaft (not shown) of an instrument and roll the shaft, such as shaft 222 of instrument 200 in the exemplary embodiment of FIG. 3, one or more flux conduits to deliver surgical flux (e.g., electrical energy, fluids, suction, light, etc.) to an end effector of an instrument, etc.

Force transmission mechanism 310 comprises one or more actuation input mechanisms 330, 332, as shown in the exemplary embodiment of FIG. 4. In an exemplary, non-limiting embodiment, actuation input mechanisms 330, 332 are capstans, as discussed above with regard to actuation input mechanisms 212, 214 of the exemplary embodiment of FIG. 3, although the use of various other actuation input mechanism configurations also is contemplated without departing from the scope of the present disclosure. Actuation elements are respectively coupled to driven actuation input mechanisms 330, 332. For example, actuation elements 340, 342 are coupled to actuation input mechanism 330 and actuation elements 344, 346 are coupled to actuation input mechanism 332, as shown in the exemplary embodiment of FIG. 4. According to an exemplary embodiment, actuation elements 340, 342, 344, 346 are tension members, such as cables, as described in U.S. Pat. Nos. 6,394,998 B1, and 8,545,515 (filed Sep. 17, 1999), which are incorporated by reference in their entirety. According to an exemplary embodiment, a pull/pull mechanism includes two tension members, with one tension member pulled to actuate an end effector or wrist in one direction and the other tension member pulled to actuate the end effector or wrist in another direction. According to another exemplary embodiment, a pull/pull mechanism includes a single tension element (e.g., a single tension element wrapped about a capstan or other actuator), with one portion of the tension element pulled to actuate an end effector or wrist in one direction and another portion of the tension member pulled to actuate the end effector or wrist in another direction. Chassis 320 of force transmission mechanism 310 has a chassis portion 322 that defines an exit aperture 324 into which actuation elements 340, 342, 344, 346 are routed. From the exit aperture 324, actuation elements 340, 342, 344, 346 are routed through the instrument shaft (e.g., shaft 222 in FIG. 3) to a distal portion of an instrument, according to an exemplary embodiment.

The actuation elements connected to a driven actuation input mechanism are formed by a single actuation element, according to an exemplary embodiment. Thus, actuation elements 340, 342 connected to actuation input mechanism 330 are formed by a single actuation element, with actuation elements 340, 342 defined by two portion of the single actuation element that extend between force transmission mechanism 310 and a distal portion of an instrument. For example, actuation elements 340, 342 are portions of a single actuation element (e.g., cable) that loops about actuation input mechanism 330 at one end in force transmission mechanism, extends from force transmission mechanism 310 through the shaft of an instrument (e.g., shaft 222 in FIG. 3), to a distal portion of an instrument (e.g., wrist 230 or end effector 220 in FIG. 3) to actuate instrument when actuation input mechanism 330 is driven. Thus, when actuation input mechanism 330 is driven, such as by being rotated along the directions indicated by arrows 331 in the exemplary embodiment of FIG. 4, one of the portions of the single actuation element (e.g., one of actuation elements 340, 342) is paid out (e.g., unwound) from actuation input mechanism 330 while the other portion of the single actuation element (e.g., the other of actuation elements 340, 342) is taken up by (e.g., wound upon) actuation input mechanism 330. Actuation elements 344, 346 connected to actuation input mechanism 332 may be similarly arranged.

According to another exemplary embodiment, each of actuation elements 340, 342 is made of two separate segments. For example, a first end of each of actuation elements 340, 342 is connected to actuation input mechanism 330 and a second end of each of actuation elements 340, 342 is connected to a distal portion of an instrument (e.g., wrist 230 or end effector 220). Actuation elements 344, 346 connected to actuation input mechanism 332 can be arranged as two separate segments of the actuation elements, according to an exemplary embodiment. Thus, actuation elements (e.g., actuation elements 340, 342 in FIG. 3) connected to an actuation input mechanism (e.g., actuation input mechanism 330 in FIG. 4) are two segments of a single actuation element, or alternatively, are defined by two actuation elements.

According to an exemplary embodiment, tension regulators of the various exemplary embodiments described herein are coupled to at least one actuation element of a force transmission mechanism either before or after the force transmission mechanism has been assembled. For example, a tension regulator is coupled to an actuation element after the actuation element has been connected to a wrist or end effector of an instrument (e.g., 230 or 220 in FIG. 3) and connected to an actuation input mechanism (e.g., 330 or 332 in FIG. 4). According to another exemplary embodiment, a tension regulator is coupled to an actuation element and then the actuation element is connected to a wrist or end effector of an instrument (e.g., 230 or 220 in FIG. 3) and connected to an actuation input mechanism (e.g., 330 or 332 in FIG. 4).

As shown in the exemplary embodiment of FIG. 4, tension regulator 350 is coupled to one or more actuation elements of force transmission mechanism 310 and is configured to passively compensate for slack in the one or more actuation elements. The tension regulator 350 may float relative to chassis 320 of force transmission mechanism 310 and thus translates freely with the actuation element to which it is coupled. Although the tension regulators 350 are shown at a location on the actuation elements 340, 346 near the input mechanisms 330, 332, the tension regulators 350 can be located on the actuation elements in any location with sufficient space for the tension regulators. For example, one or more tension regulators 350 can be located on a portion of an actuation element disposed within the surgical instrument shaft, such as within the shaft 222 of the surgical instrument 200 (FIG. 3).

Because of the way in which tension regulator 350 is coupled to an actuation element (e.g., one of actuation elements 340, 342, 344, 346), as the actuation element is wound upon or paid out from a respective actuation input mechanism (e.g., actuation input mechanism 330 or 332), such as along the directions indicated by arrows 370 in the exemplary embodiment of FIG. 4, tension regulator 350 also moves with respective actuation element to which it is coupled, along the directions indicated by arrows 370 relative to chassis 320. One consideration for such a configuration in which a tension regulator 350 is coupled to an actuation element is that as the actuation element moves back and forth between an actuation input mechanism 330, 332 and aperture 324, tension regulator 350 could contact the actuation input mechanism, or tension regulator 350 could contact chassis portion 322 in which aperture 324 is defined. Due to the size of force transmission mechanism 310 and the distance an actuation element travels between aperture 324 and actuation input mechanism 330, 332, space provided for a tension regulator 350 to travel when coupled to an actuation element is limited. In view of this, a tension regulator 350 configured to be coupled to an actuation element is designed to compensate for slack of the actuation element but also have a size small enough to minimize or eliminate impacts between the tension regulator 350 and a chassis portion 322 or an actuation input mechanism 330, 332, or other structures of the surgical instrument.

In various exemplary embodiments, a tension regulator is coupled to only one of the actuation elements connected to an actuation input mechanism (e.g., when actuation elements 340, 342 in FIG. 4 are defined by two actuation element segments) or is coupled to only one portion of an actuation element made of a single segment that extends between a force transmission mechanism and a distal portion of an instrument. But, the various exemplary embodiments described herein are not limited to such configurations and may instead have tension regulators coupled to more than one actuation element of a given actuation input mechanism. According to an exemplary embodiment, a tension regulator is coupled to each actuation element for an actuation input mechanism. Coupling of tension regulators to actuation elements can be based upon, for example, a function of a component being actuated by the actuation elements, according to an exemplary embodiment, as described in further detail below.

Figure 5:
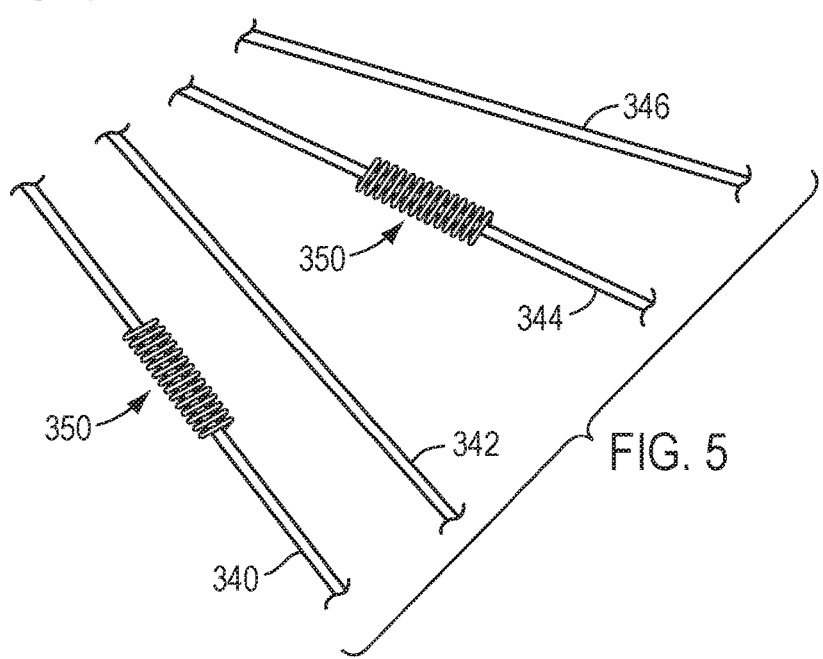
FIG. 5 is a partial, perspective view of actuation elements and tension regulators of the force transmission mechanism of FIG. 4.

As shown in the exemplary embodiment of FIG. 5, which is a partial view of actuation elements 340, 342, 344, 346 of the exemplary embodiment of FIG. 4, a tension regulator 350 is coupled to actuation element 340 but not to actuation element 342. Similarly, a tension regulator 350 is coupled to actuation element 344, but not to actuation element 346. In other words, actuation elements 342 and 346 lack tension regulators 350, as shown in FIGS. 4 and 5.

In a situation where slack is present in both actuation elements or actuation element segments associated with each actuation input mechanism (e.g., actuation elements or segments 340 and 342 associated with actuation input mechanism 330 or actuation elements or segments 344 and 346 associated with actuation input mechanism 332), precise control of end effector elements can be improved by selectively accumulating the entire slack onto only one actuation element of the actuation elements or segments associated with a particular actuation input mechanism. For example, all slack can be accumulated with a single tension regulator 350 coupled to one of actuation elements 340 and 342 or to one of actuation elements 344 and 346. Thus, all slack in actuation elements 340, 342 (or in actuation elements 344, 346) accumulates in a tension regulator 350 coupled to one of the actuation elements associated with the respective actuation input mechanism, while the other actuation element associated with the respective actuation input mechanism is drawn taut due to the removal of slack from the one actuation element via the tension regulator 350. Because the other actuation element is taut and substantially straight, the length of the other actuation element is substantially known, which facilitates precise control of an element of the surgical instrument (e.g., end effector, wrist, etc.) actuated by the actuation element.

By way of example, when tension regulator 350 is coupled to actuation element 340 and not to actuation element 342, the tension regulator 350 accumulates all slack of the paired actuation elements 340 and 342. In this way, actuation element 342 becomes taut, as indicated in FIG. 4, and the length of actuation element 342 is substantially known. Actuation input mechanism 330 (FIG. 4) can be rotated (e.g., along direction 331) by an amount corresponding to the length of actuation element 342 in order to precisely control an end effector element actuated by actuation element 342. Conversely, when the length of actuation element 342 is not substantially known, such as due to slack in actuation element 342, rotation of actuation input mechanism 330 does not necessarily provide precise control of an end effector element because the rotation of actuation input mechanism 330 is no longer matched to the length of actuation element. In other words, an amount of rotation of actuation input mechanism 330 no longer corresponds to a particular amount of paying out or winding up of actuation element 342 because slack is present in actuation element 342.

In an exemplary embodiment, tension regulators 350 in FIGS. 4 and 5 are coupled to actuation elements 340 and 344 that are pulled to actuate an end effector (e.g., end effector 220 in FIG. 3) to an open position, while actuation elements 342, 346 that are pulled to actuate the end effector to a closed position are free of tension regulators. In various exemplary embodiments, greater precision may be desirable, for example, for closing an end effector than opening the end effector. Coupling of the tension regulators 350 to the actuation elements can be selected in view of this consideration. In such an arrangement, slack is minimized or eliminated by coupling tension regulators 350 to actuation elements 340 and 344 configured to actuate the end effector to an open position, which may be accomplished with less precision and force than actuating the end effector to a closed position. Actuation elements 342 and 346 may lack tension regulators 350 but remain taut due to the removal of slack via the tension regulators 350 coupled to actuation elements 340, 344 associated with each actuation input mechanism 330, 332, respectively. Thus, the end effector can still be effectively closed in an accurate manner with a desired amount of force by tensioning actuation elements 342, 346.

According to another exemplary embodiment, a tension regulator is coupled to each actuation element associated with an actuation input mechanism. In the exemplary embodiment of FIG. 6, a partial view of actuation elements 440 and 442 connected to a single actuation input mechanism (not shown), such as actuation input mechanism 330 or 332 in the exemplary embodiment of FIG. 4, is shown. A tension regulator 450 is coupled to each of actuation elements 440 and 442 in the exemplary embodiment of FIG. 6.

Figure 6:
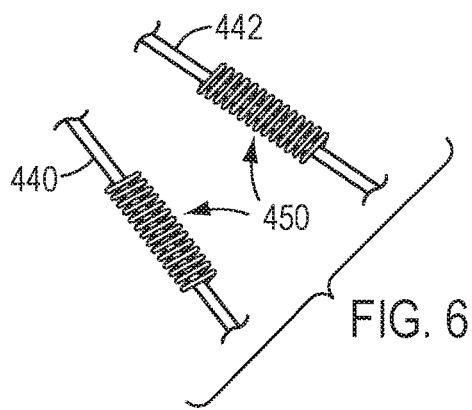
FIG. 6 is a partial perspective view of actuation elements and tension regulators according to an exemplary embodiment.

In the exemplary embodiments of FIGS. 4-6, a single tension regulator is coupled to an actuation element. However, the various exemplary embodiments described herein are not limited to a single tension regulator being coupled to an actuation element. According to other exemplary embodiments, more than one tension regulator is coupled to any one actuation element. For example, two, three, or more tension regulators are coupled to any one actuation element.

In exemplary embodiments of the disclosure, a tension regulator is configured to apply a compressive force to one or more portions of an actuation element in line with a length of the one or more portions of the actuation element. For example, in an exemplary embodiment, a tension regulator is configured to remove (e.g., compensate for) slack in an actuation element by applying a compressive force between two longitudinal locations of the actuation element resulting in a collapsing (e.g., buckling, bending, etc.) of the actuation element between the two longitudinal locations. In other words, a tensile force applied to the actuation element is partly or completely transmitted through the tension regulator between the two longitudinal locations when the actuation element is in the collapsed (e.g., bent) configuration in which it compensates for slack in the actuation element.

Figure 7:
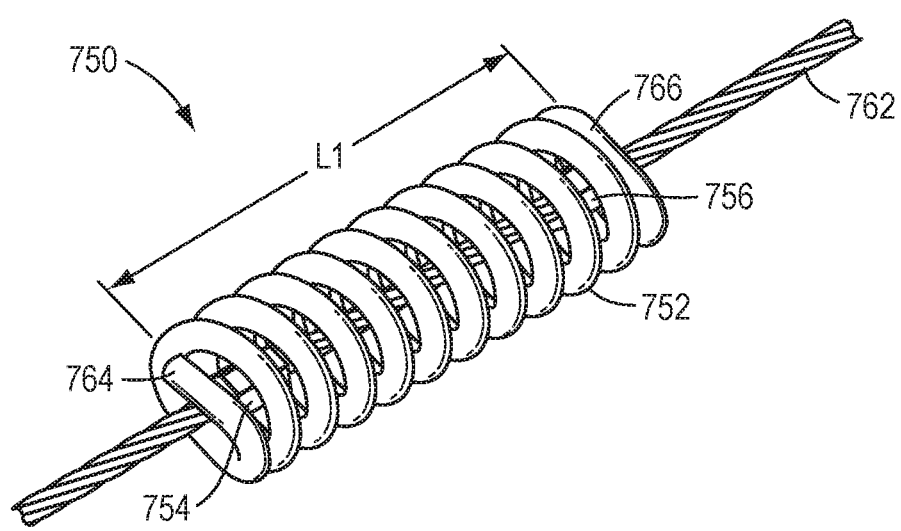
FIG. 7 is a perspective view of a tension regulator according to an exemplary embodiment in an expanded state.

For example, referring now to FIG. 7, an exemplary embodiment of a tension regulator 750 is shown. In the exemplary embodiment of FIG. 7, the tension regulator 750 includes a biasing element 752 (e.g., a spring) disposed around an actuation element 762, such as, for example, any of actuation elements 340, 342, 344, and 346 in FIG. 4. The tension regulator 750 includes stops 754 and 756 affixed at longitudinal locations on the actuation element 762 that are separated by a distance L1. In various exemplary embodiments, the stops 754 and 756 are collars or crimps affixed around the actuation element 762, for example, by crimping, soldering, brazing, welding, adhesives, etc.

The spring 752 is an "extension" type spring. In other words, the spring collapses to a first length in the absence of any applied tensile force, and extends to a second length greater than the first length under an applied tensile force. The difference in the first and second length is proportional to the magnitude of the applied tensile force. The actuation element 762 passes through the first and second ends 764, 766 of the spring 752, while the stops 754, 756 abut the first and second ends 764, 766, respectively, of the spring 752. In other words, the stops 754, 756 are too large to pass through the first and second ends 764, 766 of the spring 752. In the exemplary embodiment of FIG. 7, the first and second ends 764 and 766 of the spring 752 are bent in at least a partial loop (e.g., a hairpin bend) around the actuation element 762, such that the stops 754 and 756 and the portion of the actuation element 762 between the stops 754 and 756 are positioned within the spring 752.

The spring 752 is configured to remove slack from the actuation element 762 by bearing at least a portion of a tensile load applied to the actuation element 762. In a first position, as shown in FIG. 7, in which no slack is present in the actuation element 762, the entire actuation element 762, including the portion between the stops 754 and 756, is placed under tension, and so the spring 752 is in an extended configuration. The spring 752 is in an extended configuration, as shown in FIG. 7, when the actuation element 762 is in an unstretched (e.g., without slack development) state, and the actuation element 762 is fully extended and in a straight line between the stops 754 and 756.

As the actuation element 762 stretches (e.g., through stress cycles resulting from repeated use, etc.) slack may develop in the actuation element 762, as discussed above. As this occurs, and the state of tension in the actuation element begins to relax, the spring 752 contracts from the extended configuration shown in FIG. 7 to a partially or fully contracted configuration, such as the fully contracted configuration shown in FIG. 8, depending on the amount of slack/relaxation of the actuation element 762. As the spring 752 contracts (e.g., relaxes), the first and second ends 764 and 766 of the spring 752 apply a compressive force between the stops 754 and 756 and collapse (e.g., bend) a portion of the actuation element 762 within the spring 752, as shown in the interior cut away view of FIG. 9. In this state, the axial distance between the stops 754 and 756 is reduced to a second distance L2 shorter than the first distance L1. Bending of the actuation element 762 as shown reduces the axial distance between the stops 754 and 756, effectively reducing the length of the actuation element 762 between terminal ends (not shown in FIG. 7) of the actuation element 762 and removing slack from the actuation element 762. Stated another way, slack in the actuation element 762 is taken up inside the spring 752 as the portion of the actuation element 762 bends under the force of the spring 752. The portion of the actuation element 762 extending between the stops 754, 756 is no longer straight in this configuration, but rather follows a non-straight path.

The actuation element 762 can have a preload tension, i.e., a baseline tensile force existing in the actuation element 762 irrespective of, and in addition to, any tensile force applied to the actuation element 762, such as by the actuators 330, 332 (FIG. 4) of the force transmission mechanism 310 (FIG. 4). In exemplary embodiments, the spring 752 optionally is configured so that the tension in the spring 752 when the actuation element 762 is stretched taut (i.e., as shown in FIG. 7) is approximately equal to a preload tension of the actuation element 762. Thus, when the actuation element 762 is installed and preloaded, the spring 752 is extended and the actuation element 762 bears any force transmitted between the actuation input mechanism (e.g., actuation input mechanism 330 (FIG. 4)) and the end effector (e.g., end effector 220 (FIG. 3)). As the actuation element 762 develops slack and the spring 752 contracts (relaxes) to take up the slack, movements under loads that do not exceed the load applied by the spring 752 to the actuation element 762 do not cause the spring to extend, and the movement of the end effector 220 reflects the movement of the actuation input mechanism 330. Under heavier loads, e.g., loads that exceed the load applied by the spring 752 to the actuation element 762, the tension of the spring 752 may be overcome, the spring 752 extends, and the full load is carried by the fully extended and taut actuation element 762. Upon removal of the load, the spring 752 again contracts to eliminate any slack from the actuation element 762. Thus, the tension regulator 750 maintains tension to enable the actuation element 762 to transmit force to cause smooth, accurately controlled movement of the end effector 220.

To assemble the tension regulator 750 and the actuation element 762, the stops 754, 756 are positioned as desired and affixed to the actuation element 762. The actuation element 762 is threaded through the spring 752 prior to forming the partial loops in the ends 764, 766. The spring 752 is then extended, and ends of the spring are bent around the actuation element 762 to form the bent ends 764, 766. In some exemplary embodiments, the ends of the spring 752 may be partially bent, but not closed, leaving sufficient room for the stops 754, 756 to pass through. Once the actuation element and stops are appropriately positioned, the ends 764, 766 can be bent around the actuation element 762 to prevent stops 754,756 from passing through the ends.

Figure 8:
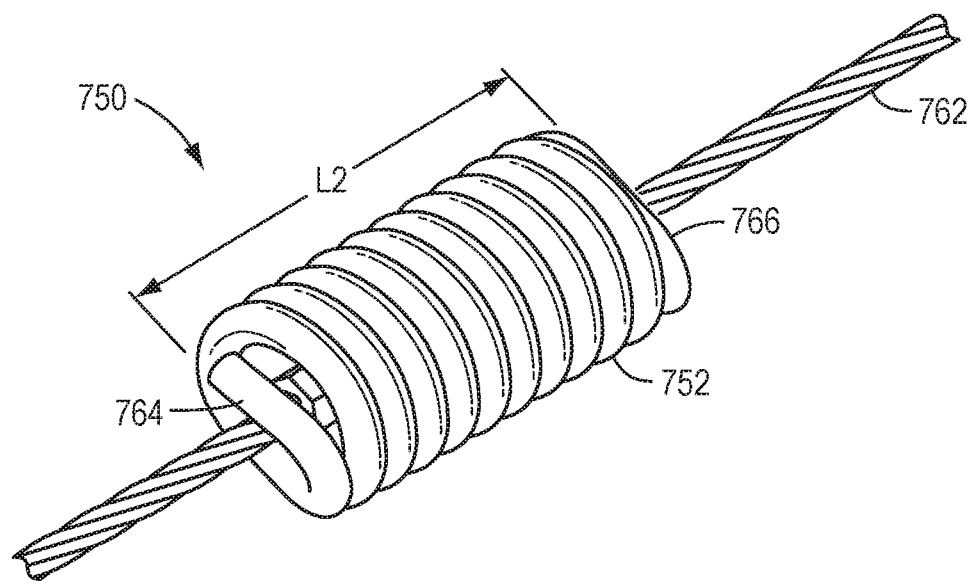
FIG. 8 is a perspective view of a tension regulator according to the exemplary embodiment of FIG. 7 in a contracted state.
Figure 9:
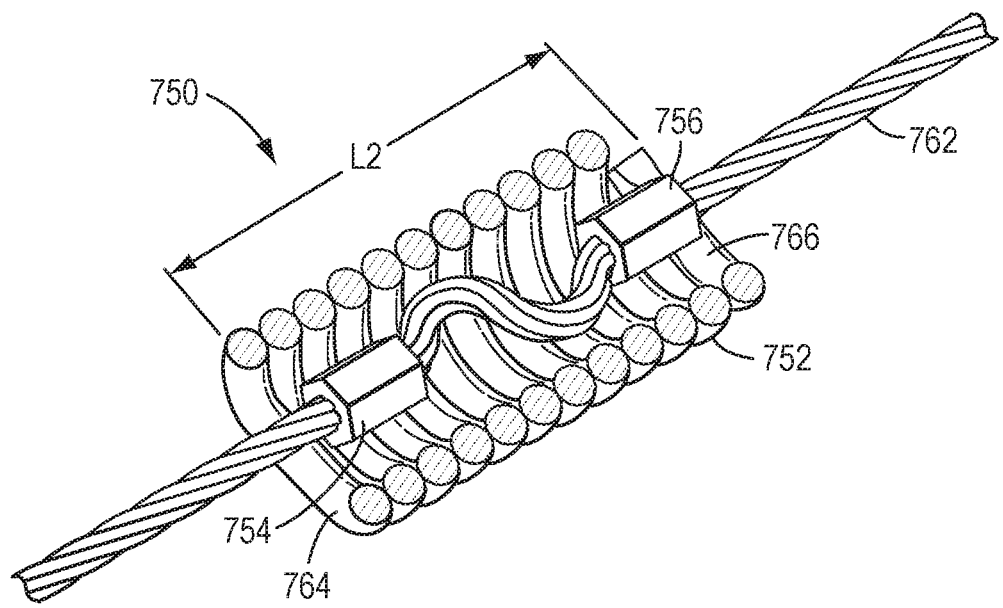
FIG. 9 is a cut away view of the tension regulator of FIG. 8.

The exemplary embodiment of FIGS. 7 through 9 is a tension regulating device with relatively few component parts (i.e., the stops 754, 756, and the spring 752), and it may enhance the overall reliability and robustness of the surgical instrument 200 (FIG. 3). Additionally, fewer overall parts may facilitate manufacture and contribute to reduced manufacturing and assembly costs compared to other configurations of tension regulators.

In some exemplary embodiments, a tension regulator is configured to apply a tensioning force to an actuation element that includes two separate segments, each of which includes an end portion, the end portions being oriented in parallel and laterally overlapping one another. The overlapping end portions each includes stops (e.g., ball ends, barrel ends) configured to engage with a tension regulating element. The tension regulating element is configured to apply a tensioning force to the laterally overlapping ends of the complementary portions of actuation elements to remove slack from the actuation element by increasing an overlap distance between the two separate segments of the actuation element.

Figure 10:
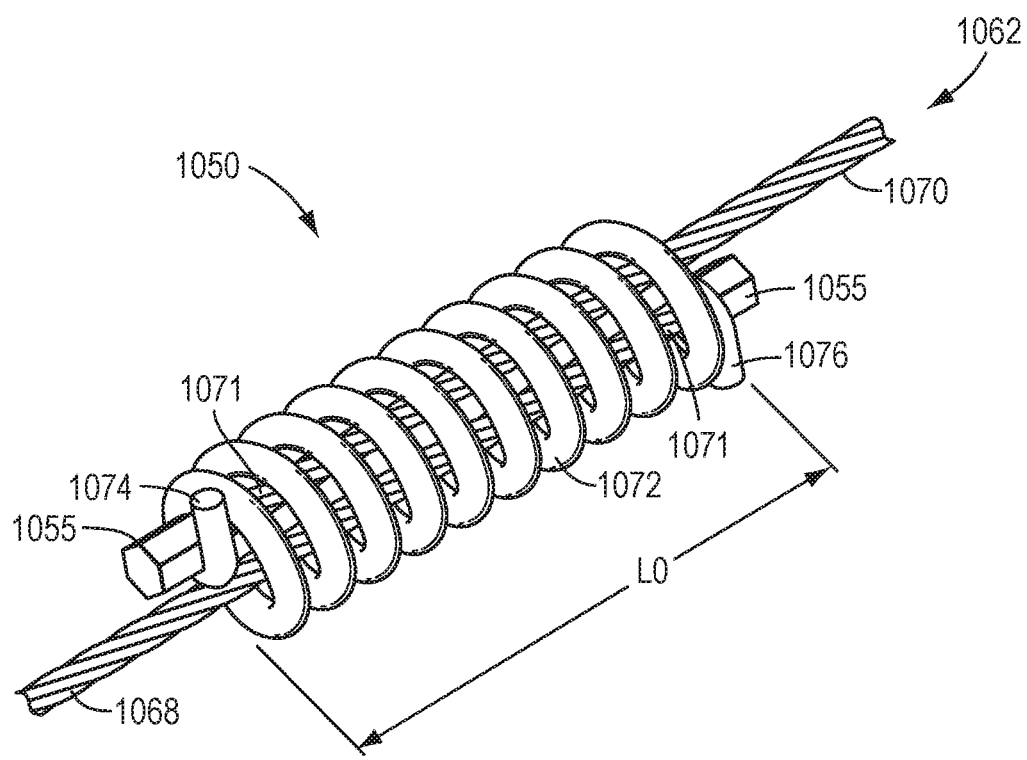
FIG. 10 is a perspective view of another tension regulator according to an exemplary embodiment.

For example, referring now to FIG. 10, an exemplary embodiment of a tension regulator 1050 is shown. In the exemplary embodiment of FIG. 10, an actuation element 1062 comprises a first segment 1068 and a second segment 1070. By way of example, the first segment 1068 is operatively coupled with, e.g., an actuation input mechanism such as actuation input mechanism 330 as discussed in connection with FIG. 4, and the second segment 1070 is operatively coupled with a portion of a surgical instrument to be actuated, such as, an end effector or wrist (e.g., the end effector 220 as discussed above in connection with FIG. 3).

Each of the first segment 1068 and second segment 1070 includes a first end (not shown) and a second end 1071. For example, the first end of the first segment 1068 is coupled with an actuation input mechanism (such as actuation input mechanism 330 or 332 (FIG. 5), and the first end of the second segment 1070 is coupled with, e.g., end effector 220 to actuate the end effector 220.

Second ends 1071 of each of the first segment 1068 and the second segment 1070 terminate at the tension regulator 1050 with an enlarged end (e.g., a barrel end or ball end) 1055. The tension regulator 1050 includes a compression spring 1072. The compression spring 1072 assumes a fully extended (e.g., expanded) configuration in the absence of an applied compressive force. When subjected to a compressive force, the compression spring 1072 contracts (e.g., shortens) by an amount proportional to the magnitude of the applied compressive force. The compression spring 1072 includes first and second ends 1074, 1076 respectively, bent around the first and second segments 1068 and 1070 of the actuation element 1062. The spring 1072 may be fully compressed when the actuation element 1062 is new and unstretched. For example, in the fully compressed position, individual coils of the spring 1072 contact one another, and the spring 1072 transfers tensile force as a solid structure (e.g., as a rod).

Second ends 1071 of the first and second segments 1068 and 1070 of the actuation element 1062 overlap one another a distance LO along a longitudinal direction of the actuation element 1062 as shown in FIG. 10. In other words, the second ends 1071 of each of the first and second segments 1068 and 1070 of the actuation element 1062 are positioned laterally adjacent to one another along a portion of the length of the second ends 1071, as shown in FIG. 10.

As one or both of the first and second segments 1068 and 1070 of the actuation element 1062 stretch and develop slack (e.g., through use including repeated stress cycles, etc.) the compression spring 1072 extends from the fully compressed state (not shown) to the state shown in FIG. 10, i.e., to an at least partially extended state. The tension regulator 1050 compensates for any extra length due to stretching of the first and second segments 1068 and 1070 by increasing the length of the overlap LO between the first and second segments 1068 and 1070 of the actuation element 1062, thus compensating for slack and maintaining the tension of the actuation element 1062.

Figure 11:
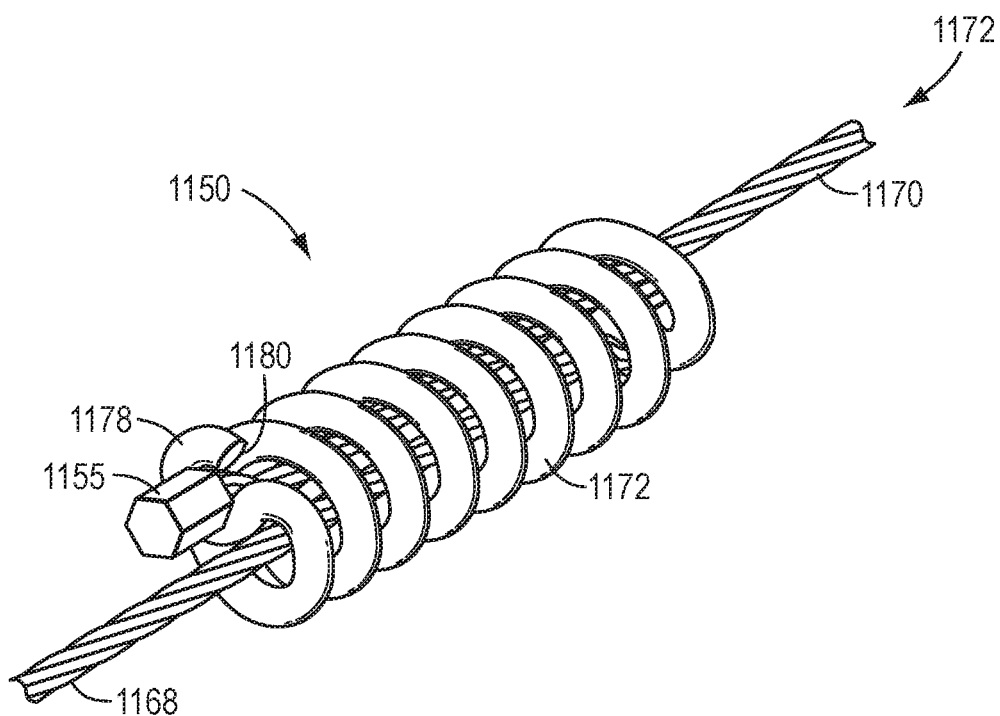
FIG. 11 is a perspective view of another tension regulator according to an exemplary embodiment.

FIG. 11 shows a tension regulator 1150 according to yet another exemplary embodiment. As with the exemplary embodiment of FIG. 10, an actuation element 1162 includes a first segment 1168 and a second segment 1170 that are separate from each other. Each segment 1168, 1170 has a barrel end 1155. The tension regulator 1150 includes a compression spring 1172, ends 1178 of which are bent with an "S"-shaped configuration. The S-shape of the bend of the ends 1178 may provide support to the barrel end 1155 around greater than 180° of the barrel end 1155. Due to the S-shape configuration of the bend of the ends 1178, terminal portions 1180 of the coil forming the spring 1172 turn inward. The turned-in terminal portions 1180 of the spring 1172 in the configuration of FIG. 11 may mitigate (e.g., prevent) interference with internal components of the force transmission mechanism 310 (FIG. 4) as the tension regulator 1150 moves with the actuation element 1172 within the force transmission mechanism.

Figure 12:
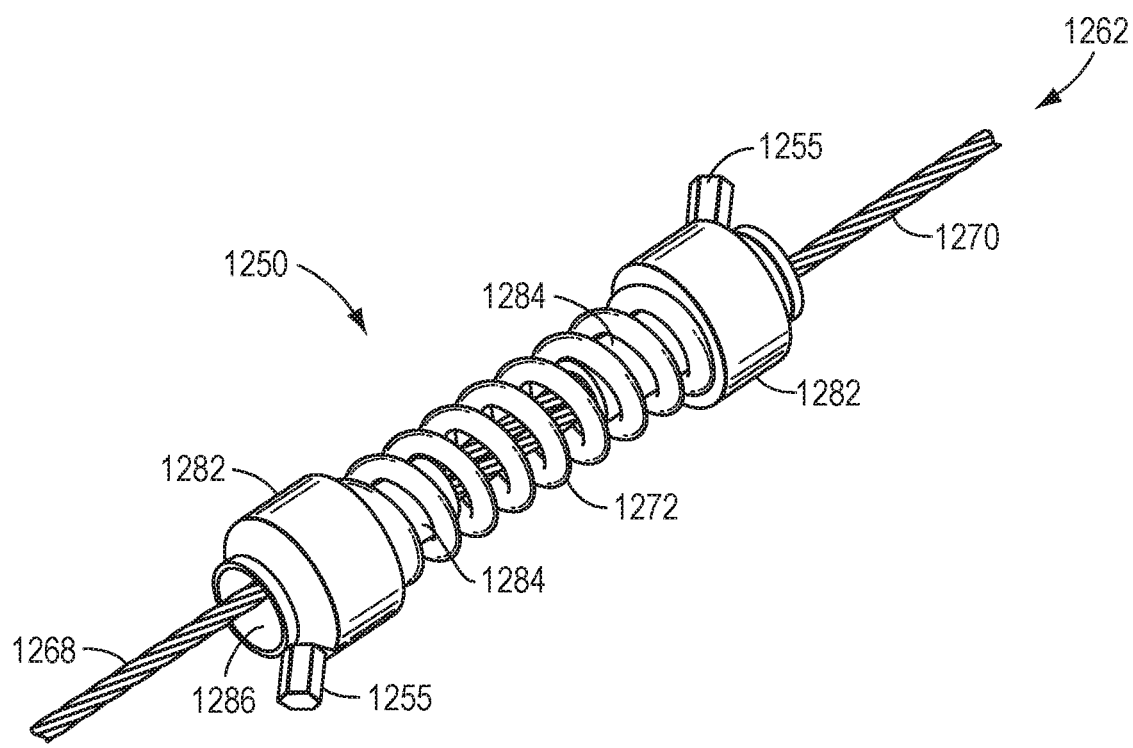
FIG. 12 is a perspective view of yet another tension regulator according to an exemplary embodiment.
Figure 13:
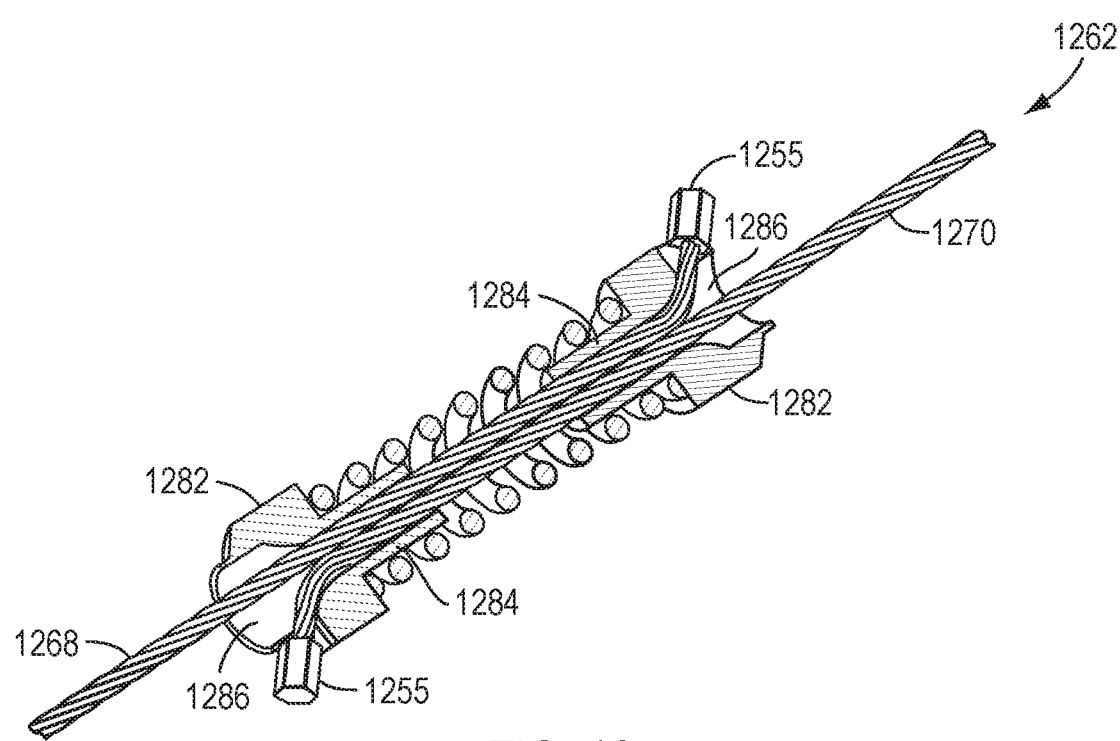
FIG. 13 is a cross-sectional view of the tension regulator of FIG. 12.

FIGS. 12 and 13 illustrate another exemplary embodiment of a tension regulator 1250 according to the present disclosure. An actuation element 1262 includes a first segment 1268 and a second segment 1270. Each of the first segment 1268 and the second segment 1270 terminates with a barrel end 1255. The tension regulator 1250 includes a compression spring 1272 disposed between first and second end caps 1282. The first and second end caps 1282 each include an inner sleeve 1284 around which a portion of the compression spring 1272 is disposed. The inner sleeves 1284 may have an outer diameter approximately equal to an inner diameter of the compression spring 1272. The inner sleeves 1284 also may have an inner diameter approximately equal to twice a diameter of each of the first segment 1268 and the second segment 1270 of the actuation element 1262 so as to allow the overlapping portions of those segments to be received in the passage defined by the spring 1272. The first and second end caps 1282 include openings 1286 through which the first segment 1268 and the second segment 1270 of the actuation element 1262 pass, while the barrel ends 1255 on the first segment 1268 and the second segment 1270 transfer a tensile force applied to the actuation element 1262 into the first and second end caps 1282 and the compression spring 1272.

The actuation element 1262 optionally is installed with a preload tension sufficient to compress the compression spring 1272 so that the inner sleeves 1284 of each of the first and second end caps 1282 contact one another. When the actuation element segments 1268, 1270 are unstretched and taut (e.g., have not developed slack), the tension regulator 1250 is compressed and acts as a solid structure (e.g., rod), transmitting tensile force directly between the first segment 1268 and the second segment 1270 of the actuation element 1262. As the first and second segments 1268 and 1270 of the actuation element 1262 stretch and develop slack, the compression spring 1272 extends, drawing overlapping portions of the first and second segments 1268 and 1270 of the actuation element 1262 past each other, as discussed above in connection with the exemplary embodiments of FIGS. 10 and 11. The end caps 1282 may facilitate relative movement between the first and second segments 1268 and 1270 of the actuation element 1262 as the overlap length changes due to slack in the actuation element 1262. For example, the first and second segments 1268 and 1270 can slide through the inner sleeves 1284 while experiencing relatively less friction compared to, e.g., the embodiments of FIGS. 10 and 11.

Although tension regulators of the various exemplary embodiments contemplated herein have been described with reference to actuation elements within a force transmission mechanism of a surgical instrument, tension regulators of the various exemplary embodiments described herein are not limited to use with a force transmission mechanism of an instrument. For example, tension regulators of the various exemplary embodiments described herein are capable of being coupled to actuation elements of a patient side cart of teleoperated surgical system. According to an exemplary embodiment, tension regulators of the various exemplary embodiments described herein can be coupled to actuation elements (e.g., tension elements) used to actuate manipulator arms 110-113 of patient side cart 100 of the exemplary embodiment of FIG. 1. Thus, tension regulators of the various exemplary embodiments described herein may be coupled to actuation elements within manipulator arms 110-113, not only to actuation elements located within force transmission mechanism 134 of FIG. 1. In addition, the tension regulators of the various exemplary embodiments described herein may be used in any type of remotely actuated instrument that does or does not include computer assisted telepresence. For example, the tension regulators of the exemplary embodiments described herein may be used with manually operated remotely actuated surgical, or other remotely-controlled (e.g., steerable) and/or actuatable instruments.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements and/or dimensions of those elements and materials, may be substituted for those illustrated and described herein, parts and processes may be reversed, and certain features of the present disclosure may be utilized independently, all as would be apparent to one skilled in the art after having the benefit of the description herein. Changes may be made in the elements described herein without departing from the spirit and scope of the present teachings and following claims.

Other embodiments in accordance with the present disclosure will be apparent to those skilled in the art from consideration of the specification and practice of the invention disclosed herein. The specification and examples should be considered as exemplary only, with the claims being entitled to their full breadth and scope, including equivalents.

What is claimed is:

1. A surgical instrument, comprising:
a shaft having a proximal end and a distal end;
a movable component coupled to the distal end of the shaft;
a force transmission mechanism coupled to the proximal end of the shaft;
an actuation element comprising a first end coupled to the force transmission mechanism, a second end coupled to the movable component, and having a continuous length extending from the first end to the second end, the actuation element being configured to transmit an actuation force from the force transmission mechanism to the movable component; and
a coil spring coupled to the actuation element at a location between the first and second ends, wherein:
first and second portions of the coil spring are coupled to first and second locations on the actuation element, the first and second locations spaced longitudinally apart from each other along the continuous length of the actuation element, and
in response to a change in tension in the actuation element, the coil spring is configured to passively expand or contract and to alter a distance between the first and second locations on the actuation element.

2. The surgical instrument of claim 1, wherein the change in tension in the actuation element comprises a change in configuration of the actuation element from taut to slack.

3. The surgical instrument of claim 1, wherein the first and second portions of the coil spring comprise bent portions configured to couple the first and second portions of the coil spring to the actuation element.

4. The surgical instrument of claim 3, wherein the actuation element further comprises first and second stop members positioned respectively at the first and second locations on the actuation element, wherein the bent portions of the first and second portions of the coil spring abut the respective first and second stop members to couple the coil spring to the actuation element.

5. The surgical instrument of claim 1, wherein:
in an expanded configuration of the coil spring, the actuation element is taut between the first and second locations on the actuation element, and
in a contracted configuration of the coil spring, a portion of the actuation element is slack between the first and second locations on the actuation element.

6. The surgical instrument of claim 5, wherein, in the contracted configuration of the coil spring, the slack in the actuation element is compensated for by an at least partially collapsed portion of the actuation element between the first and second locations on the actuation element.

7. The surgical instrument of claim 1, wherein the coil spring is configured to maintain tension in the actuation element, the tension being sufficient to transmit the actuation force from the first end of the actuation element to the second end of the actuation element.

8. The surgical instrument of claim 1, further comprising first and second end caps coupled respectively with the first and second portions of the coil spring.

9. The surgical instrument of claim 8, wherein the actuation element further comprises first and second stop members positioned respectively at the longitudinally spaced locations on the actuation element, wherein the first and second end caps abut the respective first and second stop members to couple the coil spring to the actuation element.

10. A surgical instrument comprising:
a proximal drive element;
a distal movable component;
an actuation element coupled between the proximal drive element and the distal movable component;
a first stop coupled to the actuation element at a first location;
a second stop coupled to the actuation element at a second location spaced apart from the first location, the actuation element having a continuous length extending from the first location to the second location; and
a spring having a first end engaged with the first stop, a second end engaged with the second stop, and windings that encircle the actuation element between the first and second locations.

11. The surgical instrument of claim 10:
wherein the spring is a tension spring; and
wherein the first end of the spring engaged with the first stop and the second end of the spring engaged with the second stop are engaged inside the windings of the spring.

12. The surgical instrument of claim 10:
wherein the spring is a compression spring; and
wherein the first end of the spring engaged with the first stop and the second end of the spring engaged with the second stop are engaged outside the windings of the spring.

13. The surgical instrument of claim 12:
wherein the actuation element comprises a first element and a second element, the first and second elements being separate from each other; and
wherein the first stop is coupled at an end of the first element, and the second stop is coupled at an end of the second element.

14. A surgical instrument, comprising:
a shaft comprising a proximal end and a distal end;
a movable component coupled at the distal end of the shaft;
a force transmission mechanism coupled at the proximal end of the shaft; and
a tensile actuation element comprising:
a first actuation element portion comprising a first end and a second end, the first end of the first actuation element portion being coupled to the movable component,
a second actuation element portion comprising a first end and a second end, the second end of the second actuation element portion being coupled to the force transmission mechanism, and
a coil spring comprising coils surrounding an interior space, a first end portion and a second end portion, the first end portion of the coil spring being directly coupled to the second end of the first actuation element portion, and the second end portion of the coil spring being directly coupled to the first end of the second actuation element portion,
wherein:
the first actuation element portion extends at least partially through the interior space of the coil spring,
the second actuation element portion extends at least partially through the interior space of the coil spring, and
the coil spring is in a state such that the coil spring is configured to maintain a preload tension in the tensile actuation element between the force transmission mechanism to the movable component and is configured to maintain a distance between the first end portion and the second end portion of the coil spring on a condition that actuation tension less than the preload tension is transmitted from the force transmission mechanism to the movable component.

15. The surgical instrument of claim 14, further comprising:
a first stop member disposed proximate an end of the first actuation element portion; and
a second stop member disposed proximate an end of the second actuation element portion,
wherein the first and second end portions of the coil spring comprise bent portions abutting the respective first and second stop members to affix the first and second end portions of the coil spring to the actuation element.

16. The surgical instrument of claim 14, wherein an end portion of the first actuation element portion and an end portion of the second actuation element portion are configured to laterally overlap one another.

17. The surgical instrument of claim 16, wherein the coil spring is configured to maintain tension in the actuation element by altering a distance over which the first actuation element portion and the second actuation element portion overlap.

18. The surgical instrument of claim 17, wherein the coil spring is configured to expand from a fully compressed position to an at least partially expanded position in response to tension changes caused by slack in the actuation element.

19. The surgical instrument of claim 14:
wherein the second end of the first actuation element portion extends past the first end portion of the coil spring and through the interior space of the coil spring to the second end portion of the coil spring; and
wherein the first end of the second actuation element portion extends past the second end portion of the coil spring and through the interior space of the coil spring to the first end portion of the coil spring.

* * * * *